United States Patent [19]

Evans et al.

[11] Patent Number: 4,800,212

[45] Date of Patent: Jan. 24, 1989

[54] PYRROLIDONE-2 COMPOUNDS AND ANTI-HYPERTENSIVE USE THEREOF

[75] Inventors: John M. Evans, Roydon; Geoffrey Stemp, Harlow, both of England

[73] Assignee: Beecham Group p.l.c., England

[21] Appl. No.: 742,798

[22] Filed: Jun. 10, 1985

[30] Foreign Application Priority Data

Jun. 12, 1984 [GB] United Kingdom ............... 8414987

[51] Int. Cl.[4] ............... C07D 207/27; C07D 211/76; A61K 31/40; A61K 31/435
[52] U.S. Cl. ................................. 514/424; 514/345; 546/243; 548/543
[58] Field of Search ............... 548/543, 542; 514/424, 514/345; 546/243

[56]  References Cited

FOREIGN PATENT DOCUMENTS 0051391  5/1982  European Pat. Off. .
093535  11/1983  European Pat. Off. .
2260339  9/1975  France .

Primary Examiner—Glennon H. Hollrah
Assistant Examiner—D. B. Springer
Attorney, Agent, or Firm—Jacobs & Jacobs

[57] ABSTRACT

Compounds of formula (I) or when a compound of formula (I) contain a salifiable group, a pharmaceutically acceptable salt thereof:

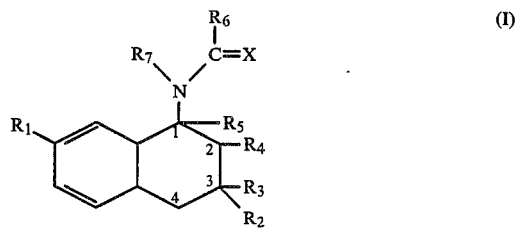

wherein: $R_1$–$R_7$ and X are as defined, are useful as antihypertensive agents.

8 Claims, No Drawings

PYRROLIDONE-2 COMPOUNDS AND ANTI-HYPERTENSIVE USE THEREOF

The present invention relates to novel di- and tetra-hydronaphthalenes having pharmacological activity, to a process and intermediates for preparing them, to pharmaceutical compositions containing them, and to their use in the treatment of animals.

U.S. Pat. Nos. 4,110,347 and 4,119,643 and 4,251,532 and European Patent Publications Nos. 28 064, 28 449, 76 075, 91 748, 93 534, 93 535 and 95 310 disclose classes of compounds that are described as having blood pressure lowering activity or anti-hypertensive activity.

A structurally distinct class of compounds has now been discovered which are di- and tetra-hydronaphthalenes substituted in the 1-position by a cyclic or acyclic amide, the nitrogen atom of the amide moiety being bonded directly to the carbon atom in the 1-position. In addition, such di- and tetra-hydronaphthalenes have been found to have blood pressure lowering activity.

Accordingly, the present invention provides a compound of formula (I) or, when the compound of formula (I) contains a salifiable group, a pharmaceutically acceptable salt thereof:

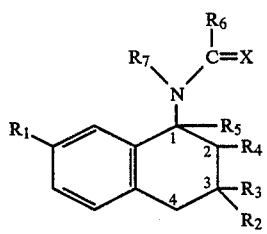

(I)

wherein:
$R_1$ is $C_{1-6}$ alkylcarbonyl, $C_{1-6}$ alkoxycarbonyl, $C_{1-6}$ alkylcarbonyloxy, $C_{1-6}$ alkylhydroxymethyl, nitro, cyano, chloro, trifluoromethyl, $C_{1-6}$ alkylsulphinyl, $C_{1-6}$ alkylsulphonyl, $C_{1-6}$ alkoxysulphinyl, $C_{1-6}$ alkoxysulphonyl, $C_{1-6}$ alkylcarbonylamino, $C_{1-6}$ alkoxycarbonylamino, $C_{1-6}$ alkyl-thiocarbonyl, $C_{1-6}$ alkoxy-thiocarbonyl, $C_{1-6}$ alkyl-thiocarbonyloxy, 1-mercapto-$C_{2-7}$ alkyl, formyl, or aminosulphinyl, aminosulphonyl or aminocarbonyl, the amino moiety being optionally substituted by one or two $C_{1-6}$ alkyl groups, or $C_{1-6}$ alkylsulphinylamino, $C_{1-6}$ alkylsulphonylamino, $C_{1-6}$ alkoxysulphinylamino or $C_{1-6}$ alkoxysulphonylamino, or ethylenyl terminally substituted by $C_{1-6}$ alkyl carbonyl, nitro or cyano;
one of $R_2$ and $R_3$ is hydrogen or $C_{1-4}$ alkyl and the other is $C_{1-4}$ alkyl or $R_3$ and $R_4$ together are $C_{2-5}$ polymethylene;
either $R_4$ is hydrogen, hydroxy, $C_{1-6}$ alkoxy or $C_{1-7}$ acyloxy and $R_5$ is hydrogen or $R_4$ and $R_5$ together are a bond;
$R_6$ is hydrogen, $C_{1-6}$ alkyl optionally substituted by halogen, hydroxy, $C_{1-6}$ alkoxy, $C_{1-6}$ alkoxycarbonyl, carboxy or amino optionally substituted by one or two independent $C_{1-6}$ alkyl groups, or $C_{2-6}$ alkenyl, amino optionally substituted by a $C_{1-6}$ alkyl or $C_{1-6}$ alkenyl group or by a $C_{1-6}$ alkanoyl group optionally substituted by up to three halo atoms, by a phenyl group optionally substituted by $C_{1-6}$ alkyl, $C_{1-6}$ alkoxy or halogen, or aryl or heteroaryl, either being optionally substituted by one or more groups or atoms selected from the class of $C_{1-6}$ alkyl, $C_{1-6}$ alkoxy, hydroxy, halogen, trifluoromethyl, nitro, cyano, $C_{1-12}$ carboxylic acyl, or amino or aminocarbonyl optionally substituted by one or two $C_{1-6}$ alkyl groups and $R_7$ is hydrogen or $C_{1-6}$ alkyl, or $R_6$ and $R_7$ together are $CH_2-(CH_2)_n-Z-(CH_2)_m-$ wherein m and n are 0 to 2 such that m+n is 1 or 2 and Z is $CH_2$, O, S or NR wherein R is hydrogen or $C_{1-6}$ alkyl;
X is oxygen or sulphur;
the nitrogen-containing group in the 1-position being trans to the $R_4$ group when $R_4$ is hydroxy, $C_{1-6}$ alkoxy or $C_{1-7}$ acyloxy.

A sub-group of $R_1$ is $C_{1-6}$ alkylcarbonyl, $C_{1-6}$ alkoxycarbonyl, nitro or cyano. Preferably, $R_1$ is $C_{1-6}$ alkylcarbonyl, such as acetyl, or is nitro or cyano.

Preferably, the alkyl groups or alkyl moieties of alkyl-containing groups for $R_1$ are methyl or ethyl.

Preferably, $R_2$ and $R_3$ are both $C_{1-4}$ alkyl, in particular both methyl.

When $R_4$ is $C_{1-6}$ alkoxy and $R_5$ is hydrogen, preferred examples of $R_4$ include methoxy and ethoxy, of which methoxy is more preferred. When $R_4$ is $C_{1-7}$ acyloxy and $R_5$ is hydrogen, a preferred class of $R_4$ is unsubstituted carboxylic acyloxy, such as unsubstituted aliphatic acyloxy. However, it is more preferred that $R_4$ and $R_5$ together are a bond, or that $R_4$ and $R_5$ are both hydrogen, or, in particular, that $R_4$ is hydroxy and $R_5$ is hydrogen.

Examples of $R_6$, when $C_{1-6}$ alkyl, include methyl, ethyl and n- and iso-propyl. Preferably such $R_6$ is methyl.

A sub-group of $R_6$, when $C_{1-6}$ alkyl substituted by halogen is $C_{1-6}$ alkyl substituted by chloro or bromo. Examples thereof include methyl or ethyl terminally substituted by chloro or bromo.

Examples of $R_6$, when $C_{1-6}$ alkyl substituted by hydroxy, include methyl or ethyl terminally substituted by hydroxy.

A sub-group of $R_6$, when $C_{1-6}$ alkyl substituted by alkoxy is $C_{1-6}$ alkyl substituted by methoxy or ethoxy. Examples thereof include methyl or ethyl terminally substituted by methoxy or ethoxy.

A sub-group of $R_6$, when $C_{1-6}$ alkyl substituted by $C_{1-6}$ alkoxycarbonyl is $C_{1-6}$ alkyl substituted by methoxycarbonyl or ethoxycarbonyl. Examples thereof include methyl or ethyl terminally substituted by methoxycarbonyl or ethoxycarbonyl.

Examples of $R_6$, when $C_{1-6}$ alkyl substituted by carboxy include methyl or ethyl terminally substituted by carboxy.

Examples of $R_6$ when alkyl substituted by amino optionally substituted to one or two independent $C_{1-6}$ alkyl groups include a group $(CH_2)_nNR_9R_{10}$ where n is 1 to 6, and $R_9$ and $R_{10}$ are each independently hydrogen or $C_{1-6}$ alkyl. Examples of n include 1 and 2, in particular 1. Preferably $R_9$ and $R_{10}$ are each independently selected from hydrogen and methyl.

Examples of $R_6$, when $C_{2-6}$ alkenyl include vinyl, prop-1-enyl, prop-2-enyl, 1-methylvinyl, but-1-enyl, but-2-enyl, but-3-enyl, 1-methylenepropyl, or 1-methylprop-2-enyl, in both their E and Z forms where stereoisomerism exists.

Examples of $R_6$ when amino optionally substituted as hereinbefore defined include a amino optionally substituted by a methyl, ethyl, propy, butyl, allyl or trichloroacetyl group or by a phenyl group optionally substituted by one methyl, methoxy or chloro group or atom, in particular amino, methylamino, and phenyl-amino optionally substituted in the phenyl ring by one methyl, methoxy or chloro group or atom.

Examples of $R_6$ when aryl include phenyl and naphthyl, of which phenyl is preferred.

A sub-group of $R_6$ heteroaryl is 5- or 6-membered monocyclic or 9- or 10-membered bicyclic heteroaryl of which 5- or 6-membered monocyclic heteroaryl is preferred. In addition, 5- or 6-membered monocyclic or 9- or 10-membered bicyclic heteroaryl preferably contains one, two or three heteroatoms which are selected from the class of oxygen, nitrogen and sulphur and which, in the case of there being more than one heteroatom, are the same or different.

Examples of 5- or 6-membered monocyclic heteroaryl containing one, two or three heteroatoms which are selected from the class of oxygen, nitrogen and sulphur include furyl, thienyl, pyrryl, oxazolyl, thiazolyl, imidazolyl and thiadiazolyl, and pyridyl, pyridazyl, pyrimidyl, pyrazyl and triazyl. Preferred examples of such groups include furanyl, thienyl, pyrryl and pyridyl, in particular 2- and 3-furyl, 2- and 3-pyrryl, 2- and 3-thienyl, and 2-, 3- and 4-pyridyl.

Examples of 9- or 10-membered bicyclic heteroaryl containing one, two or three heteroatoms which are selected from the class of oxygen, nitrogen and sulphur include benzofuranyl, benzothienyl, indolyl and indazolyl, quinolyl and isoquinolyl, and quinazonyl. Preferred examples of such groups include 2- and 3-benzofuryl, 2- and 3-benzothienyl, and 2- and 3-indolyl, and 2- and 3-quinolyl.

Preferably, the number of groups or atoms for optional substitution of aryl or heteroaryl is one, two, three or four.

Preferred examples of the groups or atoms for optional substiution of aryl or heteroaryl include methyl, methoxy, hydroxy, chloro, nitro or cyano.

A sub-group of $R_6$ is phenyl or naphthyl or a 5- or 6-membered monocyclic or a 9- or 10-membered bicyclic heteroaryl, the phenyl, naphthyl or heteroaryl group being optionally substituted by one, two, three or four groups or atoms selected from the class of $C_{1-6}$ alkyl, $C_{1-6}$ alkoxy, halogen, trifluoromethyl, nitro or cyano.

A preferred subgroup of phenyl optionally substituted as hereinbefore defined is phenyl, 4-substituted phenyl, 3-substituted phenyl, 3,4-disubstituted phenyl and 3,4,5-trisubstituted phenyl. Particular examples of phenyl optionally substituted as hereinbefore defined include phenyl, 4-hydroxyphenyl, 4-fluorophenyl, 4-cyanophenyl, 3-nitrophenyl, 3,4-dichlorophenyl and 3,4,5-trimethoxyphenyl.

A preferred sub-group of 5- or 6-membered monocyclic or 9- or 10-membered bicyclic heteroaryl optionally substituted as hereinbefore defined is unsubstituted or mono-substituted 5- or 6-membered monocyclic or 9- or 10-membered bicyclic heteroaryl, in particular unsubstituted 5- or 6-membered monocyclic or 9- or 10-membered bicyclic heteroaryl.

$R_6$ and $R_7$, when together are $CH_2$—($CH_2$)$_n$—Z—($CH_2$)$_m$-, the resulting radical substituting the di- or tetra-hydronaphthalene in the 1-position is either pyrrolidonyl or piperidonyl.

Preferred examples of $R_6$ and $R_7$ are R6 methyl and $R_7$ hydrogen and $R_6$ and $R_7$ together are $C_3$ or $C_4$ polymethylene.

Preferably, X is oxygen.

Examples of a pharmaceutically acceptable salt of a compound of formula (I), when the compound contains a salifiable group which is an optionally substituted amino group, include acid addition salts such as the hydrochloride and hydrobromide salts. Such a salifiable group may be within an $R_6$ group. A carboxy group within $R_6$ may also be salified to form metal salts, such as alkali metal salts, or optionally substituted ammonium salts.

Preferably, a compound of formula (I) is in substantially pure form.

The compounds of formula (I), wherein $R_4$ is hydrogen, hydroxy, $C_{1-6}$ alkoxy or $C_{1-7}$ acyloxy and $R_5$ is hydrogen, are asymmetric, and, therefore, can exist in the form of optical isomers. The present invention extends to all such isomers individually and as mixtures, such as racemates.

Examples of compounds of formula (I) include the compounds prepared in the Examples hereinafter.

The present invention also provides a process for the preparation of a compound of formula (I) or, when the compound of formula (I) contains a salifiable group, a pharmaceutically acceptable salt thereof, which comprises;

(i) acylating a compound of formula (II):

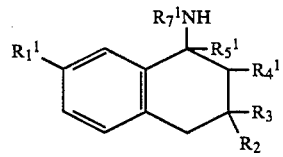

wherein $R_1^1$ is $R_1$ or a group or atom convertible thereto, $R_2$ and $R_3$ are as defined hereibefore, $R_4^1$ is hydroxy, $C_{1-6}$ alkoxy or $C_{1-7}$ acyloxy, and $R_7^1$ is hydrogen or $C_{1-6}$ alkyl, the $R_1^7NH$ group being trans to the $R_4^1$ group, (a) with an acylating agent of formula (III):

$R_8$—CO—$L_1$                   (III)

wherein $L_1$ is a leaving group, and $R_8$ is hydrogen, $C_{1-6}$ alkyl optionally substituted by halogen, hydroxy, $C_{1-6}$ alkoxy, $C_{1-6}$ alkoxycarbonyl, carboxy or amino optionally substituted as hereinbefore defined for $R_6$, $C_{2-6}$ alkenyl or optionally substituted aryl or heteroaryl a hereinbefore defined for $R_6$, or a group convertible to $R_6$ as hereinbefore defined, and thereafter, when $R_7$ is hydrogen and $R_8$ is $Z(CH_2)_zL$, where z is 3 or 4; and Z is a leaving group, cyclising the resultant compound;

(b) with a compound of formula (IV)

X=C=N.$R_{11}$                   (IV)

wherein $R_{11}$ is hydrogen, $C_{1-6}$ alkyl, $C_{1-6}$ alkenyl, $C_{1-6}$ alkanoyl optionally substituted by up to three halo atoms, or phenyl optionally substituted by $C_{1-6}$ alkyl, $C_{1-6}$ alkoxy or halogen; and X is oxygen or sulphur, and thereafter when $R_{11}$ is hydrogen, optionally converting $R_{11}$; or (ii) where, in the resultant compound of formula (I), $R_6$ and $R_7$ together are $CH_2(CH_2)_n$—Z—$(CH_2)_m$— wherein m and n are 0 to 2 such that m+n is 1 or 2 and Z is $CH_2$, O, S or NR wherein R is hydrogen or $C_{1-6}$ alkyl. and $R_4$ and $R_5$ together are a bond or each is hydrogen, reacting a compound of formula (V):

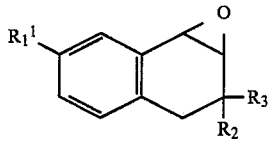

wherein $R_1^1$ is $R_1$ or a group or atom convertible thereto, $R_2$ and $R_3$ are as defined hereinbefore, with a compound of formula (VI):

$$R_{13}NHCOR_{12} \quad (VI)$$

wherein $R_{12}$ and $R_{13}$ together are $CH_2(CH_2)_n-Z-(CH_2)_m-$ wherein m and n are 0 to 2 such that m+n is 1 or 2 and Z is $CH_2$, O, S or NR wherein R is hydrogen or $C_{1-6}$ alkyl in the case where $R_1^1$ is a group or atom convertible into $R_1$, converting the group or atom into $R_1$; optionally converting $R_1$ or $R_4$ in the resulting compound into another $R_1$ or $R_4$ respectively in the case where $R_4$ and $R_5$ in the resulting compound are hydroxy and hydrogen respectively, optionally dehydrating the compound to give another compound wherein $R_4$ and $R_5$ together are a bond, and optionally reducing the resulting compound wherein $R_4$ and $R_5$ together are a bond, to give another compound, wherein $R_4$ and $R_5$ are each hydrogen; and optionally thiating the $R_7-N-CO-R_6$ group in the resulting compound to give a compound wherein X is sulphur; and when the resulting compound of formula (I) contains a salifiable group, optionally forming a pharmaceutically acceptable salt thereof.

In the process variant (i) (a) acylation of a compound of formula (II) with an acylating agent of formula (III), the leaving group $L_1$ is a group that is displaceable by a primary or secondary amino nucleophile. Examples of such a group include $C_{1-4}$ alkanoyloxy, and halogen, such as chloro and bromo. When the leaving group $L_1$ is either of these examples, the acylating agent of formula (III) is either an acid anhydride or an acid halide. When it is an acid anhydride, it may be a mixed or simple anhydride. If it is a mixed anhydride, it may be prepared in situ from a carboxylic acid and an acid halide, although this is less preferred than using the halide itself.

In process variant (i) (a), when $R_6$ in the desired compound of formula (I) is an $R_6$ optionally substituted amino-substituted alkyl group as hereinbefore defined, it is preferred that $R_8$ is a group convertible to the $R_6$ substituted alkyl group as hereinbefore defined, in particular that it is $C_{1-6}$ alkyl substituted by halo, especially bromo. The $R_8$ halo substituent in the resultant compound of process variant (i) (a) may be converted to an $R_6$ substituent which is amino optionally substituted as hereinbefore defined by a conventionaly amination reaction with ammonia or a corresponding alkyl - or dialkylamine.

Less favorably $R_8$ may be $C_{1-6}$ alkyl substituted by protected amino, protected $C_{1-6}$ alkylamino or amino substituted by two independent $C_{1-6}$ alkyl groups, it being necessary to protect the $R_8$ amino function in process variant (i) (a).

When the acylating agent of formula (III) is an acid anhydride, the acylation of the compound of formula (II) may be carried out in the presence of an acid acceptor, such as sodium acetate, optionally using the anhydride as the solvent.

When the acylating agent of formula (III) is an acid halide, the acylation of the compound of formula (II) is, preferably, carried out in a non-aqueous medium, such as dichloromethane, in the presence of an acid acceptor, such as triethylamine, trimethylamine, pyridine, picoline or calcium, potassium or sodium carbonate.

When $R_4^1$ in a compound of formula (II) is hydroxy, there is a risk of a side-reaction between the hydroxy group and the acylating agent of formula (III). However, the reaction may be carried out under controlled conditions such that only the amine, $R_7^1NH-$ is acylated, for example, by using a $C_{2-9}$ acyloxy group as the leaving group $L_1$, in the acylating agent of formula (III) in the manner as previously described for an acid anhydride, and/or effecting the reaction at relatively low temperature, e.g. at below 10° C. Alternatively $R_4^1$ may be $C_{1-7}$ acyloxy in a compound of formula (II), although less preferably if $R_4$ in the resultant compound of formula (I) is to be hydroxy, and, after reaction with the acylating agent of formula (III), be converted in hydroxy, as described hereinafter.

When $R_8$ is $Z(CH_2)_z$ where the variables are as hereinbefore defined, the leaving group Z is a group that is displaceable by a secondary amino nucleophile adjacent to a carbonyl function. A preferred example is chloro.

The cyclisation reaction when $R_8$ is $Z(CH_2)_z$ where the variables are as hereinbefore defined is preferably carried out in an inert solvent such as dimethylformamide.

In process variant (i) (b), when $R_{11}$ in a compound of formula (IV) is $C_{1-6}$ alkyl, $C_{1-6}$ alkanoyl optionally substituted as hereinbefore defined, or phenyl optionally substituted as hereinbefore defined, the reaction between the compounds of formulae (II) and (IV) is, preferably, carried out in a solvent, such as methylene chloride, at below room temperature, in particular below 10° C.

When $R_{11}$ is hydrogen, the reaction between the compounds of formulae (II) and (IV) is, preferably, carried out using a corresponding alkali metal cyanate or thiocyanate, for example that of sodium or potassium, in an optionally methanolic aqueous medium acidified with a mineral acid, such as dilute hydrochloric acid. A slightly elevated temperature such as 50° to 90° C. is apt.

In the process variant (ii) reaction of a compound of formula (V) with a compound of formula (VI), it is particularly preferred that the reaction is carried out under basic conditions so as to facilitate the formation of the anion of the compound of formula (VI), for example, in the presence of sodium hydride.

It has been found that this reaction not only brings about ring opening of the epoxide function of the compound of formula (V), but also dehydration of the product to give a compound which is, or corresponds to, a compound of formula (I) wherein $R_4$ and $R_5$ together are a bond. If it is desired to prepare a compound of formula (I) wherein $R_4$ and $R_5$ are other than a bond, subsequent conversion is necessary as hereinafter described.

Groups $R_1^1$ which are convertible into $R_1$ as hereinbefore defined and their conversion into $R_1$ are generally known in the art. They will often be a group $R_1$ in a form protected against any of the process steps, defined hereinbefore, for the preparation of a compound of formula (I) or a pharmaceutically acceptable salt thereof.

Examples of protecting agents and their addition and removal are generally known in the art.

For example, if the optional thiation reaction is to be carried out so as to obtain a compound of formula (I), wherein $R_1$ is a carbonyl-containing group and X is sulphur, it is preferred to use in the reaction of the compounds of formulae (II) and (III) or (IV), or (V) and (VI), the corresponding compound of formula (II) or (V) wherein $R_1{}^1$ is a protected carbonyl-containing group, and after thiation of the resulting compound to convert the protected carbonyl-containing group into the required carbonyl-containing group for $R_1$. Examples of preferred carbonyl protecting groups include ketalising agents, which may be added and removed in conventional manner.

Such conversions of $R_1{}^1$ groups which are convertible to $R_1$ groups may also be effected in compounds of formula (II) or intermediates thereto. For example $R_1{}^1$ bromo may be converted to cyano by reaction with copper (I) cyanide.

Examples of an optional conversion of $R_1$ in the resulting compound of formula (I) into another $R_1$ also include the optional conversion of an "-hydroxyethyl group into acetyl by oxidation, the optional conversion of an amino group into a chloro atom by the Sandmeyer reaction, or the optional conversion of a hydrogen atom into a nitro group by nitration.

The reaction of the compounds of formulae (II) and (III) or (IV) results in a compound of formula (I) wherein $R_4$ is hydroxy, $C_{1-6}$ alkoxy or $C_{1-7}$ acyloxy, whereas the reaction of the compounds of formulae (V) and (VI) results in a compound of formula (I) wherein $R_4$ is hydroxy. Examples of an optional conversion of $R_4$ in a compound of formula (I) into another $R_4$ are generally known in the art. For example, when $R_4$ is hydroxy, it may be alkylated using an alkyl iodide in an inert solvent, such as toluene, in the presence of a base, such as potassium hydroxide, or it may be acylated using a carboxylic acid chloride or anhydride in a non-hydroxylic solvent in the presence of an acid acceptor. Alternatively, when $R_4$ is $C_{1-7}$ acyloxy or $C_{1-6}$ alkoxy, it may be converted into hydroxy by conventional hydrolysis with, for example, dilute mineral acid.

The optional dehydration of the resulting compound of formula (I), wherein $R_4$ and $R_5$ are hydroxy and hydrogen respectively, into another compound of formula (I), wherein $R_4$ and $R_5$ together are a bond, may be carried out under conventional dehydration conditions, for example, by using a dehydrating agent, such as sodium hydride, in an inert solvent, such as dry tetrahydrofuran, at reflux temperature.

The optional reduction of the resulting compound of formula (I), wherein $R_4$ and $R_5$ together are a bond, into another compound of formula (I), wherein $R_4$ and $R_5$ are each hydrogen, may be carried out by hydrogenation using a catalyst of palladium on charcoal.

The optional thiation of the $R_7$—N—CO—$R_6$ group in a compound of formula (I) to give another compound of formula I, wherein X is sulphur, is, preferably, carried out with conventional thiation agents, such as hydrogen sulphide, phosporous pentasulphide and Lawesson's reagent (p-methoxyphenylthiophosphine sulphide dimer). The use of hydrogen sulphide and phosporous pentasulphide may lead to side-reactions and, therefore, the use of Lawesson's reagent is preferred.

The thiation reaction conditions are conventional for the thiation agent employed. For example, the use of hydrogen sulphide is, preferably, acid catalysed by, for example, hydrogen chloride in a polar solvent, such as acetic acid or ethanol. The preferred use of Lawesson's reagent is, preferably, carried out under reflux in a dry solvent, such as toluene or methylene chloride.

The optional formation of a pharmaceutically acceptable salt, when the resulting compound of formula (I) contains a salifiable group, may be carried out conventionally.

A compound of formula (II) may be prepared by reacting a compound of formula (V), as defined hereinbefore, with a compound of formula (VII):

$$R_7{}^1NH_2 \qquad \text{(VII)}$$

wherein $R_7{}^1$ is as defined hereinbefore; and optionally converting $R_4{}^1$ hydroxyl in the resulting compound of formula (II) into another $R_4{}^1$.

The reaction is normally carried out in a solvent, such as a $C_{1-4}$ alcohol, in particular methanol, ethanol or propanol at an ambient or an elevated temperature, for example 12° to 100° C. The reaction proceeds particularly smoothly if carried out in ethanol under reflux.

The resulting compound of formula (II) may be removed from the reaction mixture by removal of the solvent, for example, by evaporation under reduced pressure. Any epoxide impurity may be removed conventionally, for example by chromatography.

The optional conversion of the hydroxy group for $R_4{}^1$ in the resulting compound of formula (II) into a $C_{1-6}$ alkoxy or $C_{1-7}$ acyloxy group may be carried out as described hereinbefore in relation to the corresponding conversion of $R_4$ in a compound of formula (I).

A compound of formula (IV) may be prepared by reacting a compound of formula (VIII):

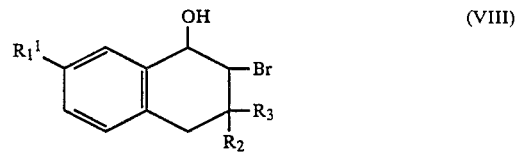

wherein $R_1{}^1$, $R_2$ and $R_3$ are as defined hereinbefore, the bromo atom being trans to the hydroxy group, with a base, such as potassium hydroxide, in a solvent, such as ether or aqueous dioxan.

A compound of formula (VIII) may be prepared by reacting a compound of formula (IX):

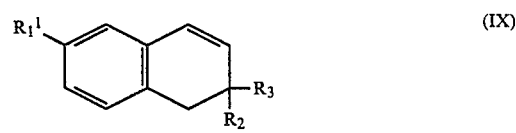

wherein $R_1{}^1$ $R_2$ and $R_3$ are as defined hereinbefore, with N-bromosuccinimide in a solvent, such as aqueous dimethyl sulphoxide.

A compound of formula (IX) may be prepared in accordance with any appropriate known process. For example, a compound of formula (IX) may be prepared by the process depicted below:

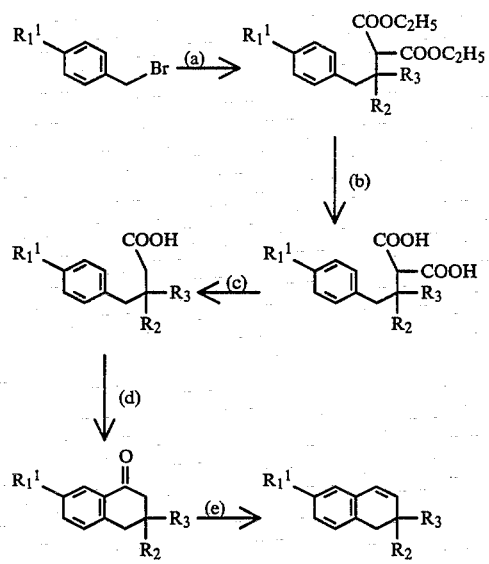

Reaction (a)

A Grignard reagent is formed from the benzyl bromide by reaction with magnesium in dry ether under reflux. The complex is then treated with copper (I) chloride and the product is then reacted with a compound of formula:

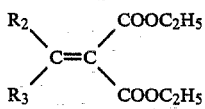

wherein $R_2$ and $R_3$ are as defined hereinbefore.

Reaction (b)

The diester is deesterified conventionally using potassium hydroxide in aqueous ethanol.

Reaction (c)

The diacid is mono-decarboxylated at an elevated temperature.

Reaction (d)

The acid is dehydrated with concomitant cyclisation using polyphosphoric acid at elevated temperatures.

Reaction (e)

The naphthalenone in dry ethanol is reduced with sodium borohydride to give the corresponding alcohol which is then treated under reflux with para-toluenesulphonic acid in benzene.

As mentioned previously, some of the compounds of formula (I) may exist in optically active forms, and the processes of the present invention produce mixtures of such forms. The individual enantiomers may be resolved by chromatography using a chiral phase.

It is preferred that the compounds of formula (I) are isolated in substantially pure form.

The intermediates of formulae (II), (V), (VIII) or (IX) are believed to be novel and represent part of the present invention. The intermediates of formulae (III), (IV), (VI) or (VII) are known and may be prepared in accordance with an appropriate known process.

As mentioned previously, the compounds of formula (I) have been found to have blood-pressure lowering activity. They are therefore useful in the treatment of hypertension.

The present invention accordingly provides a pharmaceutical composition which comprises a compound of this invention, in particular of formula (I) or a pharmaceutically acceptable salt thereof, and a pharmaceutically acceptable carrier. In particular, the present invention provides an anti-hypertensive pharmaceutical composition which comprises an anti-hypertensive effective amount of a compound of this invention, in particular of formula (I) or a pharmaceutically acceptable salt thereof, and a pharmaceutically acceptable carrier.

The compositions are preferably adapted for oral administration. However, they may be adapted for other modes of administration, for example parenteral administration for patients suffering from heart failure.

The compositions may be in the form of tablets, capsules, powders, granules, lozenges, suppositories, reconstitutable powders, or liquid preparations, such as oral or sterile parenteral solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel,hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10-60% by weight, of the active material, depending on the method of administration.

The present invention further provides a method of prophylaxis or treatment of hypertension in mammals including man, which comprises administering to the suffering mammal an anti-hypertensive effective amount of a compound of formula (I) or a pharmaceutically acceptable salt thereof.

An effective amount will depend on the relative efficacy of the compounds of the present invention, the severity of the hypertension being treated and the weight of the sufferer. However, a unit dose form of a composition of the invention may contain from 1 to 100 mg of a compound of the invention and more usually from 2 to 50 mg, for example 5 to 25 mg such as 6, 10, 15 or 20 mg. Such compositions may be administered from 1 to 6 times a day, more usually from 2 to 4 times a day, in a manner such that the daily dose is from 5 to 200 mg for a 70 kg human adult and more particularly from 10 to 100 mg.

No toxicological effects are indicated at the aforementioned dosage ranges.

The present invention further provides a compound of formula (I) or a pharmaceutically acceptable salt thereof for use in the treatment or prophylaxis of hypertension.

The following descriptions relate to the preparation of intermediates and the following examples relate to the preparation of a compound of formula (I).

All temperatures therein are in °C.

Description 1

Diethyl-2-(4-bromophenyl)-1,1-dimethyl-ethylmalonate

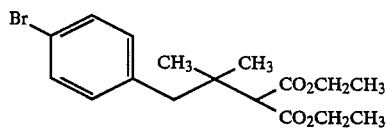

(D1)

A solution of p-bromobenzyl bromide (25.0 g) in dry ether (200 ml) was added dropwise to a suspension of magnesium turnings (2.4 g) in dry ether (50 ml), under nitrogen, such that the solvent refluxed gently. After the addition was complete, the mixture was refluxed for a further 1.5 hours, then cooled to 0° C., and cuprous chloride (0.2 g) added. The mixture was vigorously stirred for 5 minutes, and then a solution of diethyl isopropylidene malonate (15.0 g) in ether added dropwise, so that the temperature was maintained between 0°-5° C. The mixture was then allowed to rise to room temperature, and the mixture stirred for a further 1 hour, then poured into dilute sulphuric acid. The aqueous phase was extracted with ether, and the combined extracts washed successively with sodium bicarbonate solution, water, brine, then dried over sodium sulphate. Removal of solvent in vacuo, and chromatography of the residue on a silic gel column eluted with 10% ether in 60-80° C. petrol gave the required diester (17.0 g) as an oil having:

NMR (CDCl$_3$) 1.10 (s, 6H). 1.25 (t, 6H), 2.75 (s, 2H), 3.20 (s, 1H), 4.15 (q, 4H), 6.90 (d, J=8, 2H). 7.25 (d, J=8, 2H).

MH+ (C.I.) 371 (C$_{17}$H$_{23}$BrO$_4$ requires MH+ 371).

Description 2

2-(4-bromophenyl)-1,1-dimethyl-ethvlmalonic acid (D2)

A solution of diethyl-2-(4-bromophenyl)-1,1-dimethyl-ethylmalonate (17.0 g) and potassium hydroxide (17.0 g) in ethanol (100 ml) and water (50 ml) was stirred at room temperature for 48 hours. The solution was then diluted with water and extracted with ether. The aqueous phase was acidified with 5N hydrochloric acid and extracted with ethyl acetate. Drying and removal of solvent, followed by recrystallisation of the residue from acetone—60°-80° C. petrol (1:5) gave the required diacid (8.0 g) as a solid having mp 169°-173° C.;

NMR (DMSO-d$^6$) 1.10 (s, 6H), 2.80 (s, 2H), 3.10 (s, 1H), 7.00 (d, J=8, 2H), 7.30 (d, J=8, 2H), 11.50 (br, s, 2-OH).

Description 3

3,3-Dimethyl-4-(4-bromophenyl)-butanoic acid (D3)

2-(4-bromophenyl)-1,1-dimethyl-ethylmalonic acid (10.9 g) was heated in an oil bath at 200° C. for 0.5 hour, to give the required butanoic acid (9.3 g). A sample of the title compound recrystallised from 60°-80° C. petrol and had mp 81°-83° C.;

NMR (CDCl$_3$) 1.00 (2, 6H), 2.20 (s, 2H), 2.55 (s, 2H), 6.90 (d, J=8, 2H), 7.30 (d, J=8, 2H), 11.50 (s, br, OH).

M+ 270.0261 (C$_{12}$H$_{15}$BrO$_2$ requires M+ 270.0256).

Description 4

7-Bromo-3,3-dimethyl-3,4-dihydro-1(2H)-naphthalenone (D4)

A mixture of 3,3-dimethyl-4-(4-bromophenyl)-butanoic acid (9.2 g) and polyphosphoric acid (100 ml) was heated at 100° C., with occasional swirling, for 1 hour. The solution was then cooled, and water (400 ml) added cautiously. The aqueous phase was then extracted with ethyl acetate, and the combined extracts were washed with water, then brine, and dried over magnesium sulphate. Removal of drying agent and solvent gave the naphthalenone as a gum (8.2 g) having NMR (CDCl$_3$) 1.05 (s, 6H), 2.45 (s, 2H), 2.75 (s, 2H), 7.00 (d, J=8, 1H), 7.45 (dd, J=8, 2, 1H), 8.05 (d, J=2, 1H).

M+ 252.0171 (C$_{12}$H$_{12}$BrO requires M+ 252.0150).

Description 5

7-Bromo-3,3-dimethyl-1,2,3,4-tetrahydro-1-naphthol

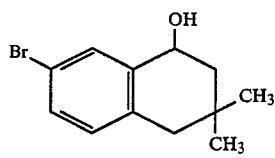

(D5)

A solution of 7-bromo-3,3-dimethyl-3,4-dihydro-1(2H)-naphthalenone (7.8 g) in dry ethanol (50 ml) at 0° C., was treated with sodium borohydride (1.5 g). The mixture was stirred and allowed to warm to room temperature over 18 hours, and the ethanol removed in vacuo. The residue was partitioned between ethyl acetate and water, and the organic layers were dried and evaporated to give the alcohol as a gum (7.0 g)

NMR (CDCl$_3$) 1.00 (s, 3H), 1.20 (s, 3H), 1.35–2.10 (m, 2H), 2.20 (s, OH̲), 2.50 (s, br, 2H), 4.80 (m, 1H), 6.90 (d, J=8, 1H), 7.20 (dd, J=8, 3, 1H), 7.65 (d, J=3, 1H).

M+ 254.0310 (C$_{12}$H$_{15}$OBr requires M+ 254.0307).

Description 6

7-Bromo-3,3-dimethyl-3,4-dihydronaphthalene

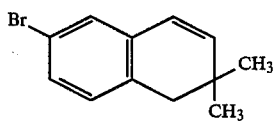

(D6)

A solution of 7-bromo-3,3-dimethyl-1,2,3,4-tetrahydro-1-naphthol (7.0 g) and p-toluene sulphonic acid (0.5 g) in benzene (100 ml) was heated under reflux, using a Dean-Stark water separator, for 1.5 hours. After cooling, solvent was removed in vacuo, and the residue partitioned between ether and water. The combined ether extracts were washed with sodium bicarbonate solution, water, brine, then dried over sodium sulphate. Removal of drying agent and solvent gave the title compound as an oil (6.2 g) having:

NMR (CDCl$_3$) 1.00 (s, 6H), 2.55 (s, 2H), 5.75 (d, J=9, 1H), 6.20 (d, J=9, 1H), 6.80–7.40 (m, 3H).

M+ 236.0209 (C$_{12}$H$_{13}$B4 requires M+ 236.0201).

Description 7

7-cyano-3,3-dimethyl-3,4-dihydronapthalene

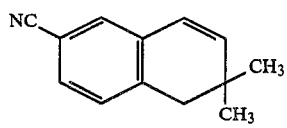

(D7)

A solution of 7-bromo-3,3-dimethyl-3,4-dihydronaphthalene (6.2 g) and copper (1) cyanide (3.5 g) in N-methylpyrrolidone (60 ml) was heated under reflux for 2 hours. After cooling, the mixture was poured into 10% aqueous ethylenediamine (200 ml) and extracted into ethyl acetate. The combined extracts were washed with water, and dried over magnesium sulphate. Solvent and drying agent were removed and the residue chromatographed on silica gel using ether-pentane (1:10) as eluant gave the dihydronaphthalene as a white crystalline solid (4.6 g), having mp 50°–52° C.;

NMR (CDCl$_3$) 1.05 (s, 6H), 2.70 (s, 2H), 5.80 (d, J=10, 1H), 6.30 (d, J=10, 1H), 7.00–7.40 (m, 3H).

M+ 183.0146 (C$_{13}$H$_{13}$N requires M+ 183.1048).

Anal. Found: C, 85.23; H, 7.14; N, 7.51; C$_{13}$H$_{13}$N requires C, 85.21; H, 7.15; N, 7.64.

Description 8

7-cyano-2-bromo-3,3-dimethyl-1,2,3,4-tetrahydro-1-naphthol

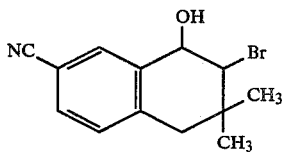

(D8)

N-Bromosuccinimide (5.0 g) was added to a vigorously stirred solution of 7-cyano-3,3-dimethyl-3,4-dihydronaphthalene (4.6 g) in dimethyl sulphoxide (50 ml) containing water (4 ml). The mixture was stirred for 1 hour at room temperature, then diluted with water and extracted into ethyl acetate. The organic extracts were washed with water and brine, then dried over sodium sulphate. Removal of drying agent and solvent gave the bromohydrin as a colourless solid (7.0 g). A sample recrystallised from 60°–80° petrol-ethyl acetate as white lustrous plates having mp 164°–165° C.;

MMR (DMSO-d$^6$) 1.00 (s, 3H), 1.20 (s, 3H), 2.85 (s, 2H), 4.10 (d, J=9, 1H), 4.30–5.50 (br, OH̲) 4.70 (d, J=9, 1H), 7.10 (d, J=8, 1H), 7.40 (d, d, J=8, 2, 1H), 7.80 (s, br, 1H).

M+ 279.0262 (C$_{13}$H$_{14}$NOBr requires M+ 279.0259).

Description 9

7-cyano-1,2-epoxy-3,3-dimethyl-1,2,3,4-tetrahydronaphthalene

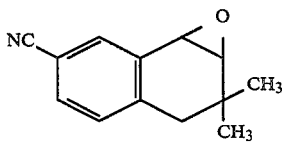

(D9)

A mixture of 7-cyano-2-bromo-3,3-dimethyl-1,2,3,4-tetrahydro-1-naphthol (7.0 g) and potassium hydroxide pellets (15.0 g) in dry ether (1 liter) was vigorously stirred at room temperature for 48 hours. The solution was filtered and evaporated in vacuo to give the epoxide (4.5 g) as a gum having:

NMR (CDCl₃) 0.85 (s, 3H), 1.35 (s, 3H), 2.20 (d,d, J=15, 2, 1H), 2.70 (d, J=15, 1H), 3.20 (d,d, J=4, 2, 1H), 3.75 (d, J=4, 1H), 7.05 (d, J=8, 1H), 7.40-7.75 (m, 2H).

M+ 199.0999 (C₁₃H₁₃NO requires M+ 199.0997).

Description 10

Trans-1-amino-3,3-dimethyl-7-cyano-1,2,3,4-tetrahydro-2-naphthol

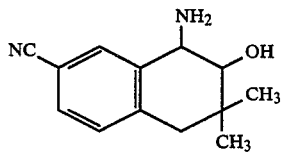

(D10)

A solution of 7-cyano-1,2-epoxy-3,3-dimethyl-1,2,3,4-tetrahydronaphthalene (3.5 g) in ethanol (50 ml) and ammonium hydroxide solution (100 ml) was stirred at room temperature for 10 days. Ethyl acetate (50 ml) was added and the mixture extracted with dilute hydrochloric acid. The acidic extracts were made basic with sodium hydroxide solution, and extracted with ethyl acetate. The organic extracts were washed with water, then brine, and dried over sodium sulphate.

Removal of drying agent and solvent gave the amino alcohol (2.0 g) as a solid having m.p. 104°-106° C.

NMR(DMSOd⁶) δ 0.80 (s,3H), 1.05 (s,3H), 2.00-3.50 (br,3H,NH₂, OH), 2.60 (s,2H), 3.10 (d,J=8,1H), 3.45 (d,J=8,1H̄), 7.15 (d,J=8,1H), 7.50 (d,d,J=8,2,1H), 7.95 (d,J=2,1H).

M+ 216.1279 (C₁₃H₁₆N₂O requires M+ 216.1263).

Example 1

7-Cyano-1-(2-oxopyrrolidinyl)-3,3-dimethyl-3,4-dihydronaphthalene (1)

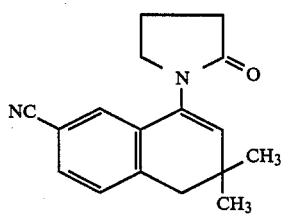

(1)

To a suspension of sodium hydride (0.18 g of 80% dispersion in oil) in dry dimethylsulphoxide (5 ml) was added 2-pyrrolidinone (0.51 g) in dimethylsulphoxide (5 ml) and the mixture was then stirred at room temperature, under nitrogen, for 1 hour. A solution of 7-cyano-1,2-epoxy-3,3-dimethyl-1,2,3,4,-tetrahydronaphthalene (1.0 g) in dimethylsulphoxide was then added dropwise, and the solution stirred for 18 hours at room temperature. The mixture was then poured into water and extracted into ethyl acetate. The combined organic layers were washed with water, then brine, and dried over sodium sulphate. Removal of drying agent and solvent, followed by chromatography of the residue on a silica gel column eluted with ethyl acetate-pentane (1:1), gave the title compound as a solid, which recrystallised from 60°-80° petrol-ethyl acetate (5:1) as yellow prisms (0.25 g) having mp 131°-2° C.;

NMR (CDCl₃) 1.10 (s, 6H), 1.90-2.70 (m, 4H), 2.70 (s, 2H), 3.60 (6, J=6, 2H), 5.80 (s, 1H), 7.00-7.40 (m, 3H).

M+ 266.1425 (C₁₇H₁₈N₂O requires M+ 266.1419)

Anal. Found: C, 76.39; H, 6.84; N, 10.40; C₁₇H₁₈N₂O requires C, 76.66; H, 6.81; N, 10.52.

EXAMPLE 2

Trans-1-acetylamino-3,3-dimethyl-7-cyano-1,2,3,4-tetrahydro-2-naphthol (2)

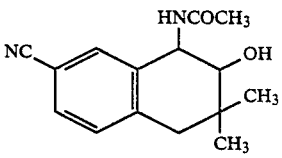

(2)

7-Cyano-1,2-epoxy-3,3-dimethyl-1,2,3,4-tetrahydronaphthalene (0.5 g) was dissolved in a mixture of ethanol (10 ml) and ammonium hydroxide solution (100 ml). The solution was stirrec at room temperature for 10 days, and then evaporated in vacuo to give the crude amino alcohol as a gum, which was dissolved in dichloromethane (75 ml) and triethylamine (0.5 ml). Acetyl chloride (0.17 ml) was then added, and the solution allowed to stand at room temperature for 36 hours. Water was added, and the organic layer separated and washed successively with 2N hydrochloric acid, sodium carbonate solution, water, brine, and then dried over sodium sulphate. Removal of drying agent and solvent, followed by recrystallisation of the residue from 60°-80° petrol-ethyl acetate (1:1) gave the title compound (0.22 g) as colourless microcrystals having m.pt. 203°-5° C.;

NMR (CDCl₃) 0.92 (s, 3H), 1.15 (s, 3H), 2.15 (s, 3H), 2.70 (s, 2H), 2.75-3.75 (OH), 3.50 (d, J=8, 1H). 5.00 (t, J=8, 8, 1H, collapsing to d, J=8, on D₂O), 6.10 (d, J=8, NH), 7.20 (d, J=8, 1H), 7.40-7.60 (m, 2H).

M+ 258.1367 (C₁₅H₁₈N₂O₂ requires M+ 258.1368.

Anal. Found: C, 69.40; H, 7.17; N, 10.37; C₁₅H₁₈N₂O₂ requires C, 69.74; H, 7.02; N, 10.84.

EXAMPLE 3

Trans-1-(2-oxo-pyrrolidinyl)-3,3-dimethyl-7-cyano-1,2,3,4-tetrahydro-2-naphthol

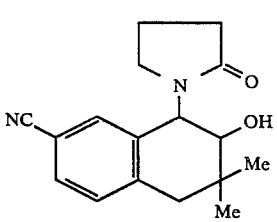

(3)

A solution of trans-1-amino-3,3-dimethyl-7-cyano-1,2,3,4-tetrahydro-2-napthol (0.5 g), triethylamine (0.5 ml) and 4-chlorobutyrylchloride (0.33 g) in dichloromethane (35 ml) was stirred at room temperature for 1 h. The solution was poured into dilute hydrochloric acid, and the organic layer separated and washed with sodium carbonate solution and dried over magnesium sulphate. Removal of drying agent and solvent gave the crude amide (0.8 g), which was not purified further, but dissolved in dry tetrahydrofuran (60 ml) and sodium hydride (75 mg of 80% dispersion in oil) added portionwise, under nitrogen. The mixture was then stirred at room temperature for 1.5 h, then poured into water and extracted into ethyl acetate. The organic extracts were washed with brine and dried over magnesium sulphate. Removal of drying agent and solvent, followed by crystallisation of the residue from ethyl acetate: 60°–80° petrol (1:1) gave the title compound as colourless microcrystals (0.35 g) having m.p. 203°–4° C.

M +284.1523 ($C_{17}H_{20}N_2O_2$ requires M+ 284.1525).

NMR (CDCl$_3$)δ0.95 (s,3H), 1.20 (s,3H), 1.95–2.30 (m,2H), 2.45 (br s,OH), 2.50–2.80 (m,4H), 2.85–3.50 (m,2H), 3.70 (d,J=10, 1H), 5.25 (d,J=10, 1H), 7.15–7.55 (m,3H).

EXAMPLE 4

Trans-1-(N-N'-methylureido)-3,3-dimethyl-7-cyano-1,2,3,4-tetrahydro-2-napthol

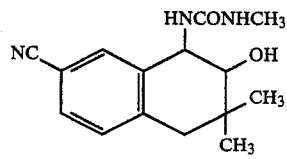

(4)

Methyl isocyanate (60 mg) was added to a solution of trans-1-amino-3,3-dimethyl-7-cyano-1,2,3,4-tetrahydro-2-naphthol (220 mg) in dichloromethane (20 ml). The solution was allowed to stand at room temperature for 3 hours, then evaporated in vacuo and the rasidue recrystallized from ethyl acetate/60°–80° petrol to give the title compound as colorless microcrystals (190 mg) having m.p. 209°–211° C.

NMR (DMSOd$^6$) δ0.90 (s, 3H), 1.15 (s,3H), 2.70 (s,2H), 2.80 (d,J=4, 3H, collapsing to singlet on D$_2$O shake), 3.45 (d,d,J=10, 2,1H, collapsing to d, J=10, on D$_2$O shake), 4.65 (d,J=2,1H, lost on D$_2$O shake), 4.75 (d,J=10,1H), 5.75 (br,1H, lost on D$_2$O shake), 6.10 (d,J=8,1H, lost on D$_2$O shake), 7.20 (d,=9,1H), 7.45 (dd,J=9,2,1H), 7.75 (d,J=2,1H).

Anal. Found: C,65.70; H, 7.15; N, 15.05; $C_{15}H_{19}N_3O_2$ requires: C, 65.91; H, 7.01; N, 15.37.

M+ 273.1479 ($C_{15}H_{19}N_3O_2$ requires M+ 273.1477).

EXAMPLE 5

Trans-1-benzoylamino-3,3-dimethyl-7-cyano-1,2,3,4-tetrahydro-2-naphthyl

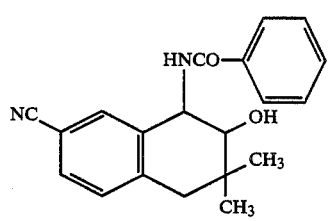

(E5)

A solution of trans-1-amino-3,3-dimethyl-7-cyano-1,2,3,4-tetrahydro-2-naphthol (220 mg), triethylamine (0.4 ml) and (145 mg) in dichloromethane (30 ml) was allowed to stand at room temperature for 18 h. The solution was poured into dilute hydrochloric acid, extracted with dichloromethane, and the organic extracts washed with sodium carbonate solution, and dried over magnesium sulphate. Removal of drying agent and solvent and crystallisation of the residue from ethyl acetate 60°–80° petrol gave the title compound as colourless needles (230 mg), having m.p. 205°–7° C.

NMR (DMSOd$^6$): 0.95 (s,3H), 1.15 (s,3H), 2.75 (m,2H), 3.75 (d,d,J=10,6,1H, collapsing to d,J=10, on D$_2$O shake) 4.75 (d,J=6,1H, lost on D$_2$O shake), 5.10 (t,1H, collapsing to d,J=10, on D$_2$O shake); 7.25 (d,J=8,1H), 7.35–7.65 (m,5H), 7.90–8.10 (m,2H), 8.60 (d,J=8,1H, lost on D$_2$O shake).

M+ 320.1530 ($C_{20}H_{20}N_2O_2$ requires M+ 320.1525)

Anal. Found: C, 74.68; H, 6.53; N, 8.29; $C_{20}H_{20}N_2O_2$. requires C, 74.98; H, 6.29; N, 8.74.

Pharmacological Data

Systolic blood pressures were recorded by a modification of the tail cuff method described by I. M. Claxton, M. G. Palfreyman, R. H. Poyser, R. L. Whiting, European Journal of Pharmacology, 37, 179 (1976). A W+W BP recorder, model 8005, was used to display pulses prior to all measurements rats were placed in a heated environment (33.5°±0.5° C.) before transfer to a restraining cage. Each determination of blood pressure was the mean of at least 6 readings. Spontaneously hypertensive rats (ages 12–8 weeks) with systolic blood pressures 170 mmHg were considered hypertensive.

| Compound of Example 1 | Time Post Dose Hours | % Change in Systolic Blood Blood | % Change in Heart Rate |
|---|---|---|---|
| 6 rats | 1* | −26 ± 3 | 0 ± 1 |
| Dose 1 mg/kg p.o. | 2 | −18 ± 3 | −6 ± 2 |
| Initial Blood Pressure | 4** | −30 ± 2 | −11 ± 3 |
| 220 ± 8 mmHg | 6 | −26 ± 4 | −7 ± 3 |
| Initial Heart Rate 517 ± 4 beats/min | 24 | 0 ± 3 | −6 ± 1 |

*At 1 hour 1 rat had no measurable pulse
**At 4 hours 2 rats had no measurable pulse

Toxicity

No toxic effects were observed in the above test.

We claim:

1. A compound of formula (I) or when the compound of formula (I) contains a salifiable group, a pharmaceutically acceptable salt thereof:

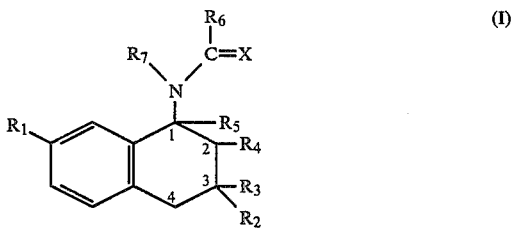

(I)

wherein:

R$_1$ is C$_{1-6}$ alkylcarbonyl, C$_{1-6}$ alkoxycarbonyl, C$_{1-6}$ alkylcarbonyloxy, C$_{1-6}$ alkylhydroxymethyl, nitro, cyano, chloro, trifluoromethyl, C$_{1-6}$ alkylsulphinyl, C$_{1-6}$ alkylsulphonyl, C$_{1-6}$ alkoxysulphinyl, C$_{1-6}$ alkoxysulphonyl, C$_{1-6}$ alkylcarbonylamino, C$_{1-6}$ alkoxycarbonylamino, C$_{1-6}$ alkylthiocarbonyl, C$_{1-6}$ alkoxy-thiocarbonyl, C$_{1-6}$ alkyl-thiocarbonyloxy, 1-mercapto-C$_{2-7}$ alkyl, formyl, or aminosulphinyl, aminosulphonyl or aminocarbonyl, the amino moiety being optionally substituted by one or two $C_{1-6}$ alkyl groups, or $C_{1-6}$ alkylsulphinylamino, $C_{1-6}$ alkylsulphonylamino, $C_{1-6}$ alkoxysulphinylamino or $C_{1-6}$ alkoxysulphonylamino, or ethylenyl terminally substituted by $C_{1-6}$ alkyl carbonyl, nitro or cyano;

one of $R_2$ and $R_3$ is hydrogen or $C_{1-4}$ alkyl and the other is $C_{1-4}$ alkyl or $R_3$ and $R_4$ together are $C_{2-5}$ polymethylene;

either $R_4$ is hydrogen, hydroxy, $C_{1-6}$ alkoxy or $C_{1-7}$ acyloxy and $R_5$ is hydrogen or $R_4$ and $R_5$ together are a bond;

$R_6$ and $R_7$ together are $CH_2\text{-}(CH_2)_n\text{-}Z\text{-}(CH_2)_m$— wherein m and n are 0 to 2 such that m+n is 1 or 2 and Z is $CH_2$;

X is oxygen or sulphur;

the nitrogen-containing group in the 1-position being trans to the $R_4$ group when $R_4$ is hydroxy, $C_{1-6}$ alkoxy or $C_{1-7}$ acyloxy.

2. A compound according to claim 1 wherein $R_1$ is acetyl, nitro or cyano.

3. A compound according to claim 1 wherein $R_2$ and $R_3$ are both methyl.

4. A compound according to claim 1 wherein $R_4$ is hydroxy and $R_5$ is hydrogen.

5. A compound according to claim 1 wherein $R_6$ and $R_7$ together are polymethylene of three or four carbon atoms.

6. A compound selected from the group consisting of:
7-Cyano-1-(2-oxopyrrolidinyl)-3,3-dimethyl-3,4-dihydro-naphthalene and
trans-1-(2-oxo-pyrrolidinyl)-3,3-dimethyl-7-cyano-1,2,3,4-tetrahydro-2-naphthol.

7. An anti-hypertensive pharmaceutical composition comprising an effective amount of a compound according to claim 1 or a pharmaceutically acceptable salt thereof and pharmaceutically acceptable carrier.

8. A method of treatment of hypertension in mammals which comprises administering to the suffering mammal an anti-hypertensive amount of a compound according to claim 1 or a pharmaceutically salt thereof.

* * * * *